(12) United States Patent
Miyaoku et al.

(10) Patent No.: US 11,466,042 B2
(45) Date of Patent: Oct. 11, 2022

(54) METHOD FOR PRODUCING FERRIC CITRATE HYDRATE

(71) Applicant: Tokuyama Corporation, Shunan (JP)

(72) Inventors: Takayuki Miyaoku, Shunan (JP); Kohei Saito, Shunan (JP)

(73) Assignee: Tokuyama Corporation, Shunan (JP)

( * ) Notice: Subject to any disclaimer, the term of this patent is extended or adjusted under 35 U.S.C. 154(b) by 0 days.

(21) Appl. No.: 16/759,401

(22) PCT Filed: Nov. 9, 2018

(86) PCT No.: PCT/JP2018/041692
§ 371 (c)(1),
(2) Date: May 12, 2020

(87) PCT Pub. No.: WO2019/093491
PCT Pub. Date: May 16, 2019

(65) Prior Publication Data
US 2020/0331943 A1     Oct. 22, 2020

(30) Foreign Application Priority Data

Nov. 10, 2017  (JP) .............................. JP2017-216856
Feb. 6, 2018   (JP) .............................. JP2018-018743

(51) Int. Cl.
*C07F 15/02*     (2006.01)

(52) U.S. Cl.
CPC .................................. *C07F 15/025* (2013.01)

(58) Field of Classification Search
None
See application file for complete search history.

(56) References Cited

U.S. PATENT DOCUMENTS

| | | | |
|---|---|---|---|
| 7,767,851 B2 * | 8/2010 | Kwok ..................... | C07F 15/02 562/590 |
| 8,093,423 B2 | 1/2012 | Chan et al. | |
| 8,299,298 B2 | 10/2012 | Chan et al. | |
| 8,338,642 B2 | 12/2012 | Kwok et al. | |
| 8,609,896 B2 | 12/2013 | Kwok et al. | |
| 8,754,257 B2 | 6/2014 | Chan et al. | |
| 8,754,258 B2 | 6/2014 | Kwok et al. | |
| 8,846,976 B2 | 9/2014 | Kwok et al. | |
| 8,901,349 B2 | 12/2014 | Kwok et al. | |
| 9,050,316 B2 | 6/2015 | Chan et al. | |
| 9,328,133 B2 | 5/2016 | Kwok et al. | |
| 9,624,155 B2 | 4/2017 | Ando et al. | |
| 9,757,416 B2 | 9/2017 | Chan et al. | |
| 9,913,821 B2 | 3/2018 | Kwok et al. | |
| 2006/0020026 A1 | 1/2006 | Kwok et al. | |

(Continued)

FOREIGN PATENT DOCUMENTS

| | | |
|---|---|---|
| JP | 4964585 B2 | 7/2012 |
| JP | 2012162522 A | 8/2012 |

(Continued)

*Primary Examiner* — Clinton A Brooks
(74) *Attorney, Agent, or Firm* — The Webb Law Firm (57) ABSTRACT

Provided is a method for efficiently producing ferric citrate hydrate with high purity and various specific surface areas. The method for producing modified ferric citrate hydrate includes a step of bringing a solution containing water, citric acid, and ferric citrate as a material into contact with water-soluble organic solvent.

12 Claims, 1 Drawing Sheet

(56) References Cited

U.S. PATENT DOCUMENTS

| | | |
|---|---|---|
| 2008/0274210 A1 | 11/2008 | Chan et al. |
| 2010/0217025 A1 | 8/2010 | Kwok et al. |
| 2012/0114747 A1 | 5/2012 | Chan et al. |
| 2012/0238622 A1 | 9/2012 | Ando et al. |
| 2013/0052261 A1 | 2/2013 | Chan et al. |
| 2013/0079537 A1 | 3/2013 | Kwok et al. |
| 2013/0345460 A1 | 12/2013 | Kwok et al. |
| 2014/0011872 A1 | 1/2014 | Kwok et al. |
| 2014/0018420 A1 | 1/2014 | Kwok et al. |
| 2014/0309298 A1 | 10/2014 | Chan et al. |
| 2015/0025138 A1* | 1/2015 | Ando .............. C07C 59/265 514/502 |
| 2015/0232495 A1 | 8/2015 | Kwok et al. |
| 2016/0095878 A1 | 4/2016 | Chan et al. |
| 2017/0095441 A1 | 4/2017 | Kwok et al. |
| 2018/0016220 A1 | 1/2018 | Ando et al. |
| 2018/0214480 A1 | 8/2018 | Chan et al. |
| 2018/0222836 A1 | 8/2018 | Smart et al. |
| 2019/0055274 A1 | 2/2019 | Kwok et al. |
| 2019/0269722 A1 | 9/2019 | Chan et al. |

FOREIGN PATENT DOCUMENTS

| | | |
|---|---|---|
| JP | 5944077 B1 | 7/2016 |
| WO | 2004074444 A2 | 9/2004 |
| WO | 2017021921 A1 | 2/2017 |

\* cited by examiner

METHOD FOR PRODUCING FERRIC CITRATE HYDRATE

CROSS-REFERENCE TO RELATED APPLICATIONS

This application is the United States national phase of International Application No. PCT/JP2018/041692 filed Nov. 9, 2018, and claims priority to Japanese Patent Application Nos. 2017-216859 and 2018-018743, filed Nov. 10, 2017 and Feb. 6, 2018, respectively, the disclosures of which are hereby incorporated by reference in their entirety.

TECHNICAL FIELD

The present invention relates to a novel method for producing ferric citrate hydrate.

BACKGROUND ART

As a method for producing ferric citrate, in existing examples ferric hydroxide is generated from ferric chloride hexahydrate with alkali such as sodium hydroxide, and include a reaction with citric acid are discussed in Japanese Patent No. 4964585 and Japanese Patent No. 5944077.

It has been known that ferric citrate is dissolved in blood and ferric ions are coupled to phosphate and a ferric phosphate compound is precipitated in an alimentary tract, so that the phosphate in blood is removed from the body and furthermore, citric acid derived from ferric citrate is converted into bicarbonate; in this manner, the symptom of a patient with kidney failure can be reduced.

On the other hand, when ferric citrate is used in the treatment for hyperphosphatemia, it is necessary to dissolve a large amount of ferric citrate in blood. In view of this, Japanese Patent No. 4964585 and Japanese Patent No. 5944077 disclose a method of obtaining amorphous ferric citrate that is dissolved with high speed and high solubility in blood in the above method. Furthermore, according to Japanese Patent No. 5944077, ferric citrate with a BET specific surface area of 20 to 45 $m^2/g$ is obtained.

Patent Literature 1: Japanese Patent No. 4964585
Patent Literature 2: Japanese Patent No. 5944077

On the other hand, it has been known that ferric citrate causes a side effect, that is, a peptic ulcer. In order to reduce the side effect, it is necessary to reduce the dose of ferric citrate, and in order to improve the dissolving speed and the solubility in blood, the specific surface area is required to be improved further. In the aforementioned producing method, in the reaction of ferric hydroxide and citric acid, the reaction occurs at high temperature of 60 to 90° C. in order to dissolve the ferric hydroxide, and the present inventors have clarified that, in this condition, citric acid partially reacts to generate a secondary product such as aconitic acid, citraconic acid, or itaconic acid. In view of the above, it is an object of the present invention to provide a producing method for efficiently obtaining ferric citrate with high purity and various specific surface areas.

For the above problem, the present inventors have made earnest researches about a method of modifying ferric citrate, and as a result, have found out that ferric citrate hydrate with high purity can be obtained by dissolving ferric citrate into water containing citric acid and then, bringing the solution into contact with water-soluble organic solvent. Through the present inventors' further examinations, it has been discovered that by adjusting the amount of water and citric acid with respect to the ferric citrate as the material when the ferric citrate is precipitated, ferric citrate hydrate with various specific surface areas can be obtained with high purity and thus, the present invention has been completed. That is to say, the present invention provides:

[1] A method for producing modified ferric citrate hydrate, the method including a step 1 of bringing a solution containing water, citric acid, and ferric citrate as a material, and a water-soluble organic solvent into contact with each other.

The present invention also provides the following preferable modes [2] to [9].

[2] The method further includes a step 1a of preparing the solution in which the ferric citrate is dissolved by dissolving the ferric citrate as the material or hydrate thereof into a citrate aqueous solution.

[3] The water-soluble organic solvent is a solvent containing at least ketone or alcohol.

[4] An amount of the water that is used is 150 to 300 mL (150 to 300 parts by volume) per 100 g (100 parts by mass) of ferric citrate monohydrate converted from the ferric citrate as the material or the hydrate thereof.

[5] An amount of the citric acid that is used is 0.05 to 1.0 moles (0.05 to 1.0 equivalents) per 1 mole (1 equivalent) of the ferric citrate monohydrate converted from the ferric citrate as the material or the hydrate thereof.

[6] An amount of the water-soluble organic solvent that is used is 300 to 4000 mL (300 to 4000 parts by volume) per 100 g (100 parts by mass) of the ferric citrate monohydrate converted from the ferric citrate as the material or the hydrate thereof.

[7] The solution is dripped into the water-soluble organic solvent.

[8] The step 1 is a step of obtaining a suspension including the modified ferric citrate hydrate, and the method further includes a step 2 of obtaining a low water content wet material of the ferric citrate containing 5 to 45 parts by mass of water per 100 parts by mass of anhydride converted from the ferric citrate hydrate from the suspension, and then drying the low water content wet material of the ferric citrate.

[9] In the step 2, after the suspension including the ferric citrate hydrate is separated into solid and liquid, the obtained wet material of the ferric citrate is dispersed in the water-soluble organic solvent and the low water content wet material of the ferric citrate containing water by 5 to 45 parts by mass per 100 parts by mass of anhydride converted from the ferric citrate hydrate is obtained.

A second aspect of the present invention is a ferric citrate hydrate having a BET specific surface area of more than 50 $m^2/g$ and 140 $m^2/g$ or less by a nitrogen adsorption method.

By a producing method according to the present invention, ferric citrate hydrate with high purity and with a low content of impurities derived from citric acid can be obtained by a simple modifying operation. Furthermore, by adjusting the amount of water and citric acid with respect to the ferric citrate as the material when the ferric citrate hydrate is precipitated, the specific surface area of ferric citrate hydrate can be controlled, and for example, ferric citrate hydrate with a BET specific surface area of more than 50 $m^2/g$ by a nitrogen adsorption method can be obtained. By the use of the ferric citrate hydrate as described above, the side effect of peptic ulcer can be suppressed and the high effect of treatment for hyperphosphatemia can be expected.

DETAILED DESCRIPTION OF EMBODIMENTS OF THE INVENTION

In some non-limiting embodiments, a method is provided for producing modified ferric citrate hydrate, the method including a step of bringing a solution containing water, citric acid, and ferric citrate as a material, preferably a solution obtained by preparing an aqueous solution of citric acid in which citric acid is contained in water and then dissolving ferric citrate as the material into the aqueous solution, and a water-soluble organic solvent in contact with each other. In the present invention, ferric citrate as the material or hydrate thereof is also referred to as "ferric citrate as the material", and ferric citrate hydrate that is modified, which is obtained after the contact of the solution with the water-soluble organic solvent, is also referred to as "modified material". The producing method according to the present invention is described below in detail.

(Ferric citrate as the material)

In the present invention, the ferric citrate as the material, which is to be dissolved in the solution, is not limited to a particular ferric citrate, and may be any ferric citrate that is commercially available as a reagent or food additive, or that is produced by a known method. Examples include methods as disclosed in Japanese Patent No. 4964585 and Japanese Patent No. 5944077. Specifically, first, ferric chloride hexahydrate is dissolved in water and then, the resulting solution is hydrolyzed using sodium hydroxide; thus, ferric hydroxide is obtained. The obtained ferric hydroxide and citric acid are subjected to reaction in water; thus, ferric citrate is generated. From the solution containing ferric citrate, ferric citrate is precipitated using an organic solvent and then separated and dried; thus, ferric citrate as the material can be produced.

Regarding the quality of the ferric citrate as the material, in the case of a commercial product, the specific surface area is usually about 0.2 to 3 $m^2/g$. The purity based on high performance liquid chromatography (HPLC) is about 65.0 to 75.0%, and aconitic acid is contained by 25.0 to 35.0%, citraconic acid is contained by 0.2 to 3.0%, and itaconic acid is contained by about 0.1 to 1.0%. On the other hand, the ferric citrate as the material, which is produced by the method disclosed in Japanese Patent No. 4964585 and Japanese Patent No. 5944077 has a specific surface area of about 16 to 45 $m^2/g$. The purity based on high performance liquid chromatography (HPLC) is about 90.0 to 98.5%, and aconitic acid is contained by 0.5 to 5.0%, citraconic acid is contained by 0.05 to 2.0%, and itaconic acid is contained by about 0.1 to 2.0%. In the producing method according to the present invention, it is possible to produce ferric citrate hydrate with the purity improved to the highest possible level as the active ingredient for the medicine even by using the ferric citrate as the material that is produced by the producing method or provided as the commercial product. In particular, it is preferable to use ferric citrate as the material with a purity by HPLC of about 90.0 to 98.5% because ferric citrate hydrate with high purity can be obtained.

(Water Containing Citric Acid)

In the producing method according to the present invention, the solution containing water, citric acid, and ferric citrate as the material is used. The solution is prepared by, preferably, dissolving ferric citrate as the material in a citrate aqueous solution in which citric acid is dissolved in water. As water contains citric acid, ferric citrate is dissolved in water with higher solubility and in addition, the purity of the modified material to be obtained is improved drastically. The citric acid to be used is not limited to particular citric acid and may be any citric acid that is industrially available. As described above, the impurities such as aconitic acid, citraconic acid, and itaconic acid contained in the ferric citrate are derived from citric acid, and from the viewpoint of obtaining ferric citrate hydrate with high purity, the impurities are preferably contained each by 0.5% or less in the citric acid.

Moreover, some citric acids are anhydride and others are hydrate; in the producing method according to the present invention, either citric acid can be used. In the case of using the hydrate as the citric acid, the net amount of citric acid excluding the hydration water may be calculated and then, the amount of water and citric acid to be used for the ferric citrate as the material may be determined. Note that the amount of water derived from the hydration water is very small with respect to the amount of water to be used as the solvent as will be described below; therefore, the amount of water derived from the hydration water does not need to be considered in determining the amount of water to be used as the solvent.

The amount of citric acid to be used may be determined as appropriate in accordance with the specific surface area of a desired modified material. In a case where the amount of water as the solvent is constant, if the amount of citric acid for the ferric citrate as the material becomes large, the specific surface area of the modified material to be obtained tends to become small, and if the amount of citric acid becomes small, the solubility of the ferric citrate as the material decreases and a large amount of water is required and thus, the yield of the modified material tends to decrease. From the viewpoints of the yield of the modified material and the purity, the citric acid is preferably used in the range of 0.05 to 1.0 moles (0.05 to 1.0 equivalents) per 1 mole (1 equivalent) of ferric citrate monohydrate converted from the ferric citrate as the material. Here, the amount of substance of the ferric citrate monohydrate converted from ferric citrate as the material is the value obtained by dividing the mass of the ferric citrate as the material by the molecular weight of the ferric citrate monohydrate with a molecular formula represented by $C_6H_5O_7.Fe.H_2O$. In addition, from the point of obtaining the modified material with a specific surface area of more than 50 $m^2/g$ in accordance with a nitrogen adsorption method, the amount of the citric acid that is used is preferably 0.1 to 0.5 moles (0.1 to 0.5 equivalents), more preferably 0.1 to 0.45 moles (0.1 to 0.45 equivalents), particularly 0.1 to 0.4 moles (0.1 to 0.4 equivalents) per 1 mole (1 equivalent) of ferric citrate monohydrate converted from the ferric citrate as the material.

On the other hand, the amount of water to be used as the solvent may be determined as appropriate in accordance with the producing scale or the specific surface area of the desired modified material. If the amount of water is small, the solution in which the ferric citrate as the material is dissolved tends to have higher viscosity and if the amount of water is large, the yield of the modified material tends to decrease. If the amount of citric acid to be used is constant, the specific surface area tends to increase as water is used less. Therefore, from the viewpoints of the workability by the increase in viscosity and the specific surface area, the water in the citrate aqueous solution per 100 g (100 parts by mass) of ferric citrate monohydrate converted from the ferric citrate as the material is preferably used in the range of 150 to 300 ml (150 to 300 parts by volume), more preferably 150 to 250 ml (150 to 250 parts by volume), and particularly preferably 170 to 250 ml (170 to 250 parts by volume). In the present invention, the amount of ferric citrate monohydrate converted from ferric citrate as the material is, in the case where the molecular formula of the ferric citrate monohydrate is expressed by $C_6H_5O_7 \cdot Fe \cdot H_2O$ (molecular weight=262.96), the amount obtained by converting the mass of the ferric citrate as the material into the mass of the ferric citrate monohydrate expressed by the above molecular formula. Specifically, in a case where the mass of the ferric citrate as the material (molecular weight=M) is a (g), the amount of the converted ferric citrate monohydrate is a×262.96/M. The molecular weight of the ferric citrate as the material can be obtained by measurement in accordance with a known method such as HPLC. In addition, if the ferric citrate as the material is a commercial product, the value written in the material specification or the like can be used as the molecular weight.

From the point of obtaining the modified material with a specific surface area of more than 50 $m^2$/g with high purity in accordance with a nitrogen adsorption method, it is particularly preferable that the amount of the citric acid that is used is 0.1 to 0.5 moles (0.1 to 0.5 equivalents) per 1 mole (1 equivalent) of the ferric citrate monohydrate converted from the ferric citrate as the material and an amount of water that is used is 150 to 220 mL (150 to 220 parts by volume) per 100 g (100 parts by volume) of the ferric citrate monohydrate converted from the ferric citrate as the material.

The citrate aqueous solution used in the producing method according to the present invention may contain another component. Specifically, the other component may be a water-soluble organic solvent such as acetone, of which 50 parts by mass or less may be used per 100 parts by mass of the citrate aqueous solution. The water-soluble organic solvent here is used separately from the water-soluble organic solvent that is brought into contact with the solution of the ferric citrate that is described below. The amount of the water-soluble organic solvent to be brought into contact with the solution of the ferric citrate is the amount that is actually used to precipitate the ferric citrate hydrate.

(Preparation of Solution)

In the producing method according to the present invention, the procedure of the dissolving operation in preparing the solution containing water, citric acid, and ferric citrate as the material is not limited to a particular procedure; however, it is preferable to include a step 1a of preparing the solution of the ferric citrate by dissolving the ferric citrate as the material into the citrate aqueous solution. It is preferable that citric acid and water are added to a vessel and stirred to prepare the citrate aqueous solution and then, ferric citrate as the material is added little by little to the aqueous solution and dissolved. The facility used for the dissolving operation is not limited to a particular facility and may be any facility that can obtain the solution of the ferric citrate. Specifically, it is preferable to use, for example, a vessel made of glass, stainless steel, Teflon (registered trademark), glass lining, or the like and moreover, for example, use a mechanical stirrer, a magnetic stirrer, or the like to stir the mixture to dissolve the ferric citrate as the material in the citrate aqueous solution because it takes shorter to dissolve and the uniformity is high. Furthermore, the solution can be prepared by adding citric acid after the ferric citrate as the material is mixed with water.

The temperature in the dissolving is not limited to a particular temperature; however, as the temperature is higher, the impurities such as aconitic acid tend to increase due to the decomposition of the ferric citrate as the material and the citric acid and as the temperature is lower, the solution has higher viscosity and tends to be solidified. For example, if the dissolving temperature is 55° C., the aconitic acid increases by about 0.1% for 30 minutes, 0.3% for 1 hour, and 0.5% for 2 hours; if the dissolving temperature is 80° C., the aconitic acid increases by about 1.5% for 30 minutes, 4.0% for 1 hour, and 8.5% for 2 hours. Therefore, from the viewpoints of the viscosity of the solution and the generation of the secondary product such as impurities, the dissolving temperature is preferably in the range of 0 to 55° C. In particular, in consideration of the time required for the dissolving and the purity of the modified material, the temperature is preferably 10 to 45° C., more preferably 15 to 40° C. The time required for the dissolving may be determined as appropriate by, for example, checking the disappearance of the ferric citrate as the material with eyes. As the solution is kept longer, the impurities such as aconitic acid derived from the citric acid and the ferric citrate as the material tend to increase. The time required for the dissolving is preferably within 2 hours. In addition, immediately after the disappearance of the solid (ferric citrate as the material) is confirmed, the solution is preferably brought into contact with the water-soluble organic solvent.

(Water-Soluble Organic Solvent)

In the present invention, the solution in which the ferric citrate is dissolved is brought into contact with the water-soluble organic solvent. Since the ferric citrate in the solution is insoluble in the water-soluble organic solvent, the ferric citrate hydrate is precipitated in the operation. The water-soluble organic solvent in the producing method according to the present invention is the organic solvent that is mixed with water in a predetermined ratio. That is to say, the water-soluble organic solvent is the organic solvent with a solubility of 20 parts by mass or more per 100 parts by mass of water at 25° C. Specific examples of the water-soluble organic solvent include alcohols such as methanol, ethanol, 1-propanol, 2-propanol, and allyl alcohol, esters such as methyl acetate, ethers such as tetrahydrofuran and dioxane, ketones such as acetone, methyl ethyl ketone, acetyl acetone, and diacetone alcohol, nitriles such as acetonitrile, and a mixed solvent thereof. Among these examples, ketones or alcohols are preferable from the viewpoints of the quality of the modified material and the yield, and particularly, acetone, 2-propanol, methanol, or ethanol is preferable. In the case of using the mixed solvent of ketone or alcohol and another solvent as the water-soluble organic solvent, the ketone or the alcohol is preferably contained by 50% by mass or more in the mixed solvent from the viewpoint of the yield.

The amount of water-soluble organic solvent to be used may be determined as appropriate in view of the capacity of production apparatus. From the viewpoints of the quality of the modified material and the yield, the amount of water-soluble organic solvent may be determined as appropriate in the range of 300 to 4000 ml (300 to 4000 parts by volume per 100 parts by mass) per 100 g of the ferric citrate monohydrate converted from the ferric citrate as the material. In particular, 300 ml (300 parts by volume) or more is preferable in point of the yield of the modified material and the solid-liquid separability, for example, and 4000 ml (4000 parts by volume) or less is preferable in point of the yield per batch. In consideration of the yield of the modified material and the solid-liquid separability, for example, 350 to 4000 ml (350 to 4000 parts by volume) is preferable, 350 to 3500 ml (350 to 3500 parts by volume) is more preferable, and 350 to 3000 ml (350 to 3000 parts by volume) is the most preferable.

(Step 1)

Step 1 is a step of bringing the solution containing water, citric acid, and the ferric citrate as the material and the water-soluble organic solvent into contact with each other. The facility used in the contact operation for the solution and the water-soluble organic solvent is not limited to a particular facility and may be, for example, a facility that is used in the production of the solution. A method of bringing the solution and the water-soluble organic solvent into contact with each other is not limited to a particular method, and after the solution is produced, the water-soluble organic solvent may be added thereto, or the solution may be added to the water-soluble organic solvent. If the water-soluble organic solvent is dripped in the solution, the ferric citrate hydrate may be easily precipitated as a block and stirring may become difficult, or the precipitated ferric citrate hydrate may adhere to the wall surface of the vessel and the yield of the modified material may decrease. Therefore, from the viewpoints of the operability and the yield, it is preferable that the solution is dripped in the water-soluble organic solvent. The dripping speed of the solution may be determined as appropriate in view of, for example, the working time or the degree of dispersion of the precipitated ferric citrate hydrate in the solvent. The time may be usually 5 minutes to 5 hours. The temperature in the contact time is preferably in the range of −20 to 50° C.; if the temperature is too low, the ferric citrate hydrate becomes a block easily and if the temperature is too high, the ferric citrate and the citric acid are decomposed to generate the impurities such as aconitic acid. In particular, in consideration of the operability such as the solid-liquid separability of the precipitated ferric citrate hydrate and the volatilization of the water-soluble organic solvent, the temperature is preferably −10 to 50° C., more preferably 0 to 40° C.

After the solution and the water-soluble organic solvent are brought into contact with each other, the mixture is preferably kept stirred for a certain period in order to precipitate the ferric citrate hydrate sufficiently. The keeping time, which is different depending on the temperature in the contact time or the like, may be usually enough in the range of 15 minutes to 50 hours. By the producing method according to the present invention as described above, a suspension containing the modified material of the ferric citrate hydrate can be obtained.

(Subsequent Operation)

The modified ferric citrate hydrate that is obtained in step 1 (that is, modified material) is separated from the suspension into solid and liquid using filtration under reduced pressure, filtration with pressure, centrifugal separation, or the like and a wet material of the modified ferric citrate hydrate is dried; thus, the modified material can be isolated. In the present invention, the wet material of the ferric citrate hydrate refers to the modified material resulting from step 1 that contains water, and the wet material containing 5 to 45 parts by mass of water per 100 parts by mass of an anhydride converted from the modified material is particularly referred to as low water content wet material. If the molecular formula of the ferric citrate anhydride is $C_6H_5O_7 \cdot Fe$ (molecular weight=244.96), the amount of anhydride converted from the modified material is the amount obtained by converting the mass of the modified material into the mass of the ferric citrate anhydride expressed by the above molecular formula. Specifically, if the mass of the modified material (molecular weight=N) is A, the amount of anhydride converted from the modified material is A×244.69/N. The molecular weight of the modified material can be obtained by a measurement in accordance with a known method. The molecular weight of the modified material can be obtained by a known method such as HPLC. To isolate the modified ferric citrate hydrate from the suspension including the modified material of the ferric citrate hydrate obtained in step 1, after the low water content wet material is obtained, step 2 of drying the low water content wet material is preferably included. It is preferable that the ferric citrate hydrate obtained in step 1 is separated from the suspension into solid and liquid using filtration under reduced pressure, filtration with pressure, centrifugal separation, or the like, and the wet material of the ferric citrate is dispersed in the water-soluble organic solvent to obtain the low water content wet material, and by drying this, the modified material is isolated. The wet material and the low water content wet material after the solid-liquid separation have the moisture absorbing property, and as the water content is increased, the crystal surface is dissolved and this may result in the decrease in specific surface area of the modified material. Depending on the condition of the drying operation for the wet material and the low water content wet material, the specific surface area may decrease in the drying operation. It is estimated that this phenomenon results from dissolving of the crystal surface of the ferric citrate hydrate with the water. In view of this, it is preferable that, in the solid-liquid separation and the drying operation, mixing of water from an external atmosphere into the wet material and the low water content wet material of the ferric citrate hydrate is suppressed. Specifically, it is preferable that the solid-liquid separation and the drying operation are performed in vacuum, in dry air atmosphere, or in inert gas atmosphere such as nitrogen or argon. In the solid-liquid separating operation, it is preferable that the wet material and the low water content wet material are cleaned with the water-soluble organic solvent or a mixed solvent with water so that a dispersant solvent (hereinafter referred to as "mother liquid") in the suspension is removed sufficiently. Note that the amount of solvent to be used in the cleaning is preferably 50 to 1000 parts by mass per 100 parts by mass of the ferric citrate monohydrate converted from the ferric citrate as the material because the cleaning effect is sufficiently achieved and the yield of the modified material is high.

Even if the mixing of moisture from the outside is suppressed as described above, in the case where the producing scale is increased, the mother liquid containing much water tends to remain in the wet material in the solid-liquid separation, and as a result, the water content in the wet material may increase and the specific surface area of the modified ferric citrate hydrate that is obtained may decrease. Therefore, in the multiple times of productions under the same condition, the modified ferric citrate hydrate that is obtained from every production may have different specific surface area. Thus, in order to suppress the decrease in specific surface area and stabilize the specific surface area of the modified ferric citrate hydrate that is obtained in every production, it is preferable that the water content in the wet material of the modified ferric citrate hydrate that is subjected to the drying operation is in a predetermined range that is less than or equal to a certain value. Specifically, the water content is preferably in the range of 5 to 45 parts by mass per 100 parts by mass of the anhydride converted from the modified ferric citrate hydrate in the wet material. In particular, from the point of suppressing the decrease in the specific surface area further, the water content is more preferably 5 to 42.5 parts by mass, more preferably 5 to 40 parts by mass, per 100 parts by mass of the anhydride converted from the modified ferric citrate hydrate that is included in the wet material. Here, the mass of the ferric citrate anhydride in the wet material can be calculated by measuring the entire weight of the wet material, the water content, and the amount of water-soluble organic solvent and then subtracting the water content and the amount of water-soluble organic solvent from the entire weight. The water content in the wet material can be measured by Karl-Fischer method. The amount of water-soluble organic solvent in the wet material can be measured by gas chromatography.

If the water content in the wet material obtained after the solid-liquid separation is 5 to 45 parts by mass per 100 parts by mass of the anhydride converted from the modified ferric citrate hydrate in the wet material, the wet material may be dried as it is. On the other hand, if the water content in the wet material is more than 45 parts by mass per 100 parts by mass of the anhydride converted from the modified ferric citrate hydrate in the wet material, it is preferable to adjust the water content to be in the range of 5 to 45 parts by mass. From the point of removing the moisture in the wet material easily, the adjusting method is preferably a method that can disperse the wet material of the modified ferric citrate hydrate, which is obtained after the solid-liquid separation, in the water-soluble organic solvent, that is, reslurry cleaning.

One example of the apparatus that is used for the reslurry cleaning may be any facility that can obtain the suspension of the modified ferric citrate hydrate. Specifically, it is preferable that a vessel made of glass, stainless steel, Teflon (registered trademark), glass lining, or the like is used and moreover, a mechanical stirrer, a magnetic stirrer, or the like is used for stirring, from the point of the efficiency of removing the moisture and the uniformity.

The procedure of the reslurry cleaning is not limited to a particular procedure; however, in point of the uniformity, it is preferable that while the water-soluble organic solvent is added to the vessel and the mixture is stirred, the wet material is added little by little to obtain the suspension.

The water-soluble organic solvent used in the reslurry cleaning (hereinafter also referred to as "reslurry water-soluble organic solvent") is preferably the organic solvent in which the solubility of the ferric citrate is low and which is mixed with water in an arbitrary ratio. Specific examples include alcohols such as methanol, ethanol, 1-propanol, 2-propanol, and allyl alcohol, esters such as methyl acetate, ethers such as tetrahydrofuran and dioxane, ketones such as acetone, methyl ethyl ketone, acetyl acetone, and diacetone alcohol, nitriles such as acetonitrile, and a mixed solvent thereof. Among these, ketones and alcohols are preferable from the viewpoint of the efficiency of removing the moisture and the yield, and acetone and ethanol are particularly preferable in point of obtaining the ferric citrate with high purity. If the mixed solvent of the ketone or alcohol and another solvent is used as the reslurry water-soluble organic solvent, it is preferable that the ketone or alcohol is contained in the mixed solvent by 50% by mass or more from the viewpoint of the yield. The amount of the reslurry water-soluble organic solvent to be used may be determined as appropriate in view of the capacity of the producing apparatus, for example, and may be in the range of 200 to 3000 ml (200 to 3000 parts by volume) per 100 g (100 parts by mass) of the converted modified ferric citrate monohydrate. The amount is preferably 200 ml (200 parts by volume) or more in point of the yield of the modified material, the solid-liquid separability, and the efficiency of removing the moisture in the wet material, and is preferably 3000 ml (3000 parts by volume) or less in point of the yield per batch. In the above-described range, the amount is preferably 300 to 2500 ml (300 to 2500 parts by volume), more preferably 400 to 2500 ml (400 to 2500 parts by volume), and the most preferably 500 to 2000 ml (500 to 2000 parts by volume) in consideration of the yield of the modified material and the efficiency of removing the moisture in the wet material. The reslurry water-soluble organic solvent may contain water by 1 part by mass or less per 100 parts by mass of the water-soluble organic solvent.

The temperature of the reslurry cleaning is preferably in the range of −20 to 50° C.; if the temperature is too low, the modified ferric citrate hydrate becomes a block easily and if the temperature is too high, the modified ferric citrate hydrate is decomposed to generate the impurities such as aconitic acid. In consideration of the operability of the solid-liquid separation and the boiling point of the water-soluble organic solvent, the temperature is preferably 0 to 40° C., more preferably 15 to 30° C. After the wet material and the reslurry water-soluble organic solvent are mixed, it is preferable to keep the mixture stirred for a certain period in order to remove the moisture from the wet material sufficiently. The mixture may be kept usually for 15 minutes to 60 minutes, which is enough, although the time depends on the temperature or the like in the cleaning. When the wet material and the reslurry water-soluble organic solvent are brought into contact, both are preferably kept in the dry air atmosphere or the inert gas atmosphere such as nitrogen or argon in order to suppress the mixing of moisture from the outside into the wet material.

The suspension including the modified ferric citrate hydrate and the reslurry water-soluble organic solvent obtained by the reslurry cleaning operation may be separated into solid and liquid by using the filtration with pressure, centrifugal separation, or the like. In order to suppress the mixing of moisture from the external atmosphere into the wet material of the modified ferric citrate hydrate, in the case of the filtration with pressure, pressure is applied using inert gas such as nitrogen or argon, and in the case of centrifugal separation, the moisture absorption is suppressed by blowing the wet material with the inert gas. In the solid-liquid separation, the wet material is preferably cleaned using the reslurry water-soluble organic solvent so as to remove the mother liquid sufficiently. The amount of solvent to be used in the cleaning is preferably 50 to 1000 parts by mass per 100 parts by mass of the ferric citrate monohydrate converted from the ferric citrate as the material because the cleaning effect is sufficiently achieved and the yield of the modified material is high.

The water content in the wet material obtained by the above operation is measured and if the wet material is the low water content wet material containing water by 5 to 45 parts by mass per 100 parts by mass of the anhydride converted from the modified ferric citrate hydrate in the wet material, the wet material may be dried as it is. On the other hand, if the water content in the wet material is more than 45 parts by mass per 100 parts by mass of the anhydride converted from the ferric citrate hydrate in the wet material, the reslurry cleaning may be repeated until the water content becomes 5 to 45 parts by mass.

The low water content wet material of the modified material can isolate the modified material free of the water-soluble organic solvent by drying under normal pressure or reduced pressure, or in the aeration of inert gas such as nitrogen or argon. The drying temperature is −80° C. or more and less than 60° C., and the time is usually 0.5 to 100 hours although the time may be determined as appropriate in consideration of the residue of the reslurry water-soluble organic solvent or the like. In the drying process, if the block shape is formed and the efficiency of reducing the reslurry water-soluble organic solvent or the like is low, the wet material is made into powder using a hammer mill, a pin mill, or the like; in this case, the drying can be performed more efficiently.

(Ferric Citrate Hydrate)

By the producing method according to the present invention described above, the ferric citrate hydrate with large specific surface can be produced with high purity. In the producing method according to the present invention, by adjusting the amount of citric acid and water, the ferric citrate hydrate with various specific surfaces, specifically a BET specific surface area by a nitrogen adsorption method in the range of more than 50 $m^2/g$ (preferably 60 $m^2/g$ or more) and 140 $m^2/g$ or less can be obtained. As a result, the solubility of the ferric citrate hydrate is higher than that of the conventional ferric citrate hydrate and in the use as the medicine, the dose of the ferric citrate hydrate can be reduced. Furthermore, the impurities derived from the citric acid, such as aconitic acid, are contained less and the purity is high; therefore, this ferric citrate hydrate can be used suitably as the medicine or food additives. In addition, the ferric citrate hydrate with a BET specific surface area of more than 50 $m^2/g$ is superior to the ferric citrate hydrate with a BET specific surface area of 50 $m^2/g$ or less in the separability in separating the ferric citrate from the suspension into solid and liquid. For example, in the case of the ferric citrate hydrate with a BET specific surface area of more than 50 $m^2/g$ in the scale of 50 g of the ferric citrate as the material, the solid-liquid separating using the pressure filter takes 5 minutes. On the other hand, in the case of the ferric citrate hydrate with a BET specific surface area of 50 $m^2/g$ or less, it takes 20 minutes, and thus, this difference exhibits the superiority from the industrial point of view. Since the separability is high, the mother liquid does not remain in the wet material of the modified material after the solid-liquid separation and thus, the modified material can have higher purity. In addition, the wet material containing less liquid can be dried more efficiently. The reason is not clarified but is considered because of the grain size distribution of the modified material or the difference in bulk density.

Specifically, the ferric citrate hydrate of more than 50 $m^2/g$ usually has a bulk density of 1.0 $g/cm^3$, and the ferric citrate hydrate of 50 $m^2/g$ or less, for example, 45 $m^2/g$ or less usually has a bulk density of 2.5 $g/cm^3$. Because of the difference in physical property as described above, the ferric citrate hydrate according to the present invention is superior in solid-liquid separability, is easily handled in the production of medicine, and is superior in mixing or compression molding, for example.

EXAMPLES

Non-limiting embodiments of the present invention are hereinafter described in detail with reference to examples.

The purity of ferric citrate or hydrate thereof according to Examples and Comparative examples, and the amount of impurities such as aconitic acid were measured in accordance with the high performance liquid chromatography (HPLC). In addition, the specific surface area of ferric citrate as the material and the modified ferric citrate hydrate according to Examples and Comparative examples was measured in accordance with a nitrogen adsorption method. The water content in the wet material of the modified ferric citrate hydrate according to Example was measured in accordance with the Karl-Fischer method. The amount of water-soluble organic solvent in the wet material of the modified ferric citrate hydrate in Example was measured in accordance with the gas chromatography (GC). The device used in each measurement and the conditions in the measurement are as below.

(Purity, Impurity Amount)

The purity of, and the amount of impurities in the ferric citrate or hydrate thereof in accordance with the HPLC were measured under the following condition:

Device: liquid chromatograph device (Waters Corporation)

Detector: UV absorption photometer (Waters Corporation)

Measurement wavelength: 210 nm

Column: a stainless steel tube with an inner diameter of 4.6 mm and a length of 250 mm filled with octadecyl silylated silica gel for liquid chromatography for 5 μm Mobile phase: mixed liquid in which 12.0 g of sodium dihydrogen phosphate is added to 2000 mL of water and dissolved therein, and then phosphate is added thereto so that the mixture has a pH of 2.2

Flow rate: 1.0 mL per minute

Column temperature: constant temperature around 30° C.

Measurement time: 30 minutes

In the HPLC analysis by the condition, the ferric citrate as the material and the modified ferric citrate hydrate maintain the citric acid for about 6.6 minutes. In Examples and Comparative examples below, the purity of the ferric citrate as the material and the modified ferric citrate hydrate is the ratio of the peak area value of the citric acid to the total of the area values of all the peaks (except the peaks derived from iron and solvent) measured in the above condition. On the other hand, the time for keeping the impurities is about 11.9 minutes for the aconitic acid, about 12.7 minutes for the itaconic acid, and the citraconic acid for about 16.1 minutes. In Examples and Comparative examples below, the amount of each impurity is the ratio of the peak area value of each impurity to the total of the area values of all the peaks (except the peaks derived from iron and solvent) measured in the above condition.

(Specific surface area)

Regarding the specific surface area of the ferric citrate as the material and the modified ferric citrate hydrate in Examples and Comparative examples below, the nitrogen adsorption amount at a nitrogen dispersion pressure in the range of 0.1 to 0.3 under the condition below was measured and from the dispersion pressure and the nitrogen adsorption amount, the specific surface area was analyzed and calculated in accordance with the BET method.

Device: specific surface area measurement device (MicrotracBEL Corp.)

Measurement method: constant-volume nitrogen adsorption method

Amount of sample: about 100 mg

Preprocessing temperature: 40° C.

Preprocessing time: 1 hour (Water content)

In Examples below, the water content in the wet material of the modified ferric citrate hydrate was measured under the condition below.

Device: Water content measurement device (Mitsubishi Chemical Corporation)

Measurement method: Karl-Fischer volumetric titration method

Titrating agent: SS-Z (Mitsubishi Chemical Corporation)

Solvent: anhydrous methanol

Amount of sample: about 15 mg

The average value from three measurements under the above condition was used as the water content.

(Amount of Water-Soluble Organic Solvent)

The amount of water-soluble organic solvent in the wet material of the modified ferric citrate hydrate in accordance with the gas chromatography (GC) was measured under the condition below.

Device: gas chromatograph device (Agilent Technologies, Inc.)

Detector: flame ionization detector (Agilent Technologies, Inc.)

Column: fused silica tube with an inner diameter of 0.53 mm and a length of 30 m having an inner surface covered with polyethylene glycol for gas chromatography with a thickness of 1 μm Column temperature: 50° C. for 6 minutes after injection, and then temperature increased up to 220° C. by 40° C. every minute and maintained for 5 minutes at 220° C.

Column pressure: 3 psi

Injection temperature: 250° C.

Detector temperature: 250° C.

Carrier gas: helium

Split: 1/10

Head space heating temperature: 90° C.

Head space heating time: 30 minutes

In Examples below, the amount of water-soluble organic solvent in the wet material of the modified ferric citrate hydrate is the ratio of the mass of the water-soluble organic solvent to the mass of the wet material of the modified ferric citrate hydrate in accordance with a calibration method, that is calculated from the peak area value of the water-soluble organic solvent that is measured in the above condition.

Preparation Example

Production of Ferric Citrate as Material

The ferric citrate as the material used in Examples and Comparative examples below was produced in accordance with the method below. To a four-neck flask of 5 L, including a mixing impeller and a thermometer, 400.0 g (1480 mmol) of iron chloride hexahydrate and 1600 mL of water were added and stirred. Next, an aqueous solution containing 177.6 g (4440 mmol) of sodium hydroxide and 1600 mL of water was dripped for 3 hours at 0 to 10° C., so that a reaction solution was prepared. Next, after the reaction solution was stirred for 1 hour at 0 to 10° C., the crystal was separated by centrifugal separation and the crystal was cleaned twice with 100 mL of water. Subsequently, the obtained crystal and 2000 mL of water were added and the mixture was stirred for 1 hour at 0 to 10° C. The crystal was separated by centrifugal separation and the crystal was cleaned twice with 100 mL of water. In addition, the obtained crystal and 2000 mL of water were added and the mixture was stirred for 1 hour at 0 to 10° C. The crystal was separated by centrifugal separation and the crystal was cleaned twice with 100 mL of water. Thus, 942.1 g of a wet material of ferric hydroxide was obtained.

To a four-neck flask of 5 L, including a mixing impeller and a thermometer, 369.6 g (1924 mmol) of anhydrous citric acid and 480 mL of water were added and stirred. Thus, a citrate aqueous solution was prepared. Next, to the citrate aqueous solution, 942.1 g of the wet material of ferric hydroxide obtained as above was added and the mixture was stirred for 30 minutes at 20 to 30° C. for reaction. Furthermore, the temperature of the reaction solution was increased up to about 80° C., and the solution was stirred for 2 hours at 75 to 85° C. After the solution was cooled to about 25° C., the insoluble substance was removed by filtration through a PTFE filter with a pore size of 0.5 μm; thus, the filtrate was obtained. To 8000 mL of acetone, the obtained filtrate was dripped for 30 minutes at 20 to 30° C. After the mixture was stirred for 1 hour at 20 to 30° C., the crystal was separated by centrifugal separation and the crystal was cleaned twice with 400 mL of acetone. The wet material obtained after the cleaning was dried under reduced pressure for 15 hours at 30° C., and thus 330.8 g of the ferric citrate hydrate as the material was obtained. If the molecular weight of ferric citrate monohydrate is 262.96, it is 1258 mmol, and the yield based on the mole number of ferric chloride hexahydrate was 85.0%. The BET specific surface area of the ferric citrate as the material by a nitrogen adsorption method was 30.0 m$^2$/g. The HPLC purity of the ferric citrate was 98.06%, the aconitic acid was 0.91%, the citraconic acid was 0.09%, the itaconic acid was 0.12%, and the other impurities were 0.18% at maximum.

Example 1

To a four-neck flask of 1 L, including a mixing impeller and a thermometer, 8.04 g (41.8 mmol) of anhydrous citric acid and 68 mL of water were added and stirred. Thus, a citrate aqueous solution was prepared. Next, to the citrate aqueous solution, 40.0 g (152.1 mmol (assuming that the molecular weight is 262.96)) of the ferric citrate monohydrate as the material obtained in the above preparation example was added little by little for 15 minutes and the mixture was stirred. After the mixture was stirred for 1 hour at 25 to 35° C., it was confirmed that the entire amount of ferric citrate hydrate was dissolved and the solution was formed. To 800 mL of acetone, the obtained solution was dripped for 30 minutes at 20 to 30° C. After the mixture was stirred for 1 hour at 20 to 30° C., the precipitated crystal was separated by centrifugal separation and the crystal was cleaned twice with 40 mL of acetone; thus, the wet material was obtained. The obtained wet material had a water content of 13.2% and an acetone content of 59.2%, and the water content per 100 parts by mass of the anhydride converted from the ferric citrate hydrate (100 parts by mass of pure ferric citrate) was 47.8 parts by mass. The wet material was dried under reduced pressure for 15 hours at 30° C., and thus 36.4 g of the modified ferric citrate hydrate was obtained. If the molecular weight of ferric citrate monohydrate is 262.96, it is 138.3 mmol, and the yield based on the mole number of the converted ferric citrate monohydrate as the material was 90.9%. The BET specific surface area of the ferric citrate hydrate by the nitrogen adsorption method was 84.4 m$^2$/g. In addition, the HPLC purity of the ferric citrate hydrate was 99.95%, and the aconitic acid was 0.03%, the citraconic acid and the itaconic acid were not detected, and the other impurities were 0.01% at maximum.

Examples 2 to 10, 30, and 31, and Comparative Example 1

Figure 1:
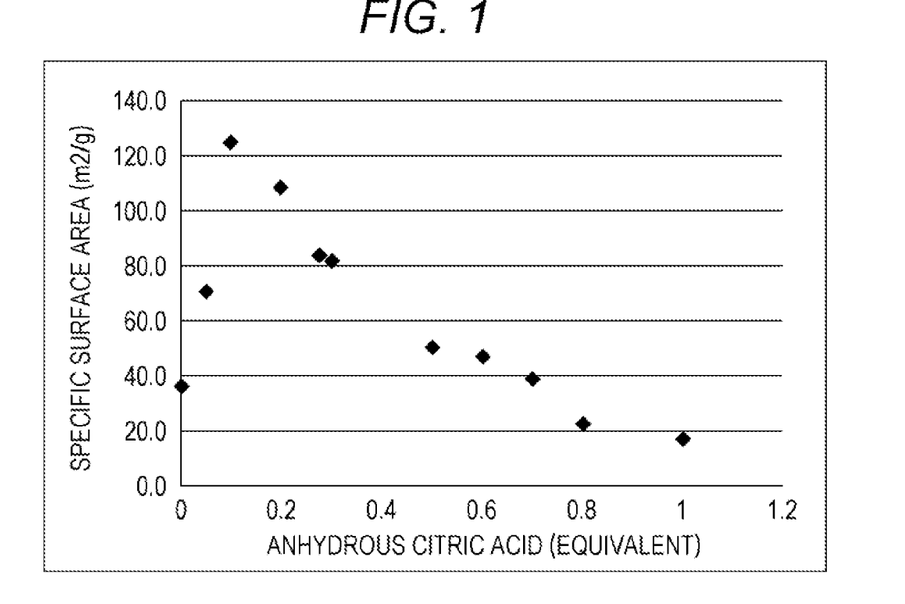
FIG. 1 is a graph showing a relation between the amount of citric acid and the specific surface area of the obtained ferric citrate hydrate in a producing method according to non-limiting embodiments of the present invention.

Examples 2 to 10, 30, and 31, and Comparative example 1 were performed in a manner similar to Example 1 except that the amount of anhydrous citric acid was changed. The conditions and results are shown in Table 1. The number of equivalents of citric acid to the ferric citrate as the material and the result of the specific surface area, which are plotted, are shown in FIG. 1.

TABLE 1

|  | Anhydrous citric acid | | Modified ferric citrate hydrate (modified material) | | | | | |
| --- | --- | --- | --- | --- | --- | --- | --- | --- |
|  | Amount used (g) | Amount converted (mol) * | Specific surface area (m$^2$/g) | Purity (%) | Aconitic acid (%) | Itaconic acid (%) | Citraconic acid (%) | Recovery rate (%) |
| Ferric citrate as material | — | — | 30.0 | 98.06 | 0.91 | 0.12 | 0.09 | — |
| Example 1 | 8.04 | 0.275 | 84.4 | 99.95 | 0.04 | Not detected | Not detected | 90.6 |
| Example 2 | 1.46 | 0.05 | 71.2 | 99.89 | 0.09 | Not detected | 0.02 | 89.5 |
| Example 3 | 2.92 | 0.1 | 125.2 | 99.91 | 0.08 | Not detected | Not detected | 90.3 |
| Example 4 | 5.84 | 0.2 | 108.9 | 99.92 | 0.06 | Not detected | Not detected | 90.5 |
| Example 5 | 8.77 | 0.3 | 82.2 | 99.95 | 0.04 | Not detected | Not detected | 90.9 |
| Example 6 | 14.61 | 0.5 | 50.6 | 99.95 | 0.04 | Not detected | Not detected | 91.1 |
| Example 7 | 17.58 | 0.6 | 47.5 | 99.95 | 0.04 | Not detected | Not detected | 91.0 |
| Example 8 | 20.46 | 0.7 | 39.2 | 99.95 | 0.05 | Not detected | Not detected | 91.1 |
| Example 9 | 23.38 | 0.8 | 22.9 | 99.95 | 0.04 | Not detected | Not detected | 90.8 |
| Example 10 | 29.22 | 1 | 17.2 | 99.95 | 0.04 | Not detected | Not detected | 90.9 |
| Example 30 | 0.58 | 0.02 | 60.3 | 99.94 | 0.04 | Not detected | Not detected | 88.5 |
| Example 31 | 35.1 | 1.2 | 13.2 | 99.82 | 0.1 | 0.0 | 0.0 | 91.3 |
| Comparative example 1 | — | — | 36.6 | 98.54 | 0.54 | 0.07 | 0.09 | 70.2 |

* Per 1 mole of ferric citrate monohydrate converted from ferric citrate as material Examples 11 to 17, and 32 and Comparative Example 4

Figure 2:
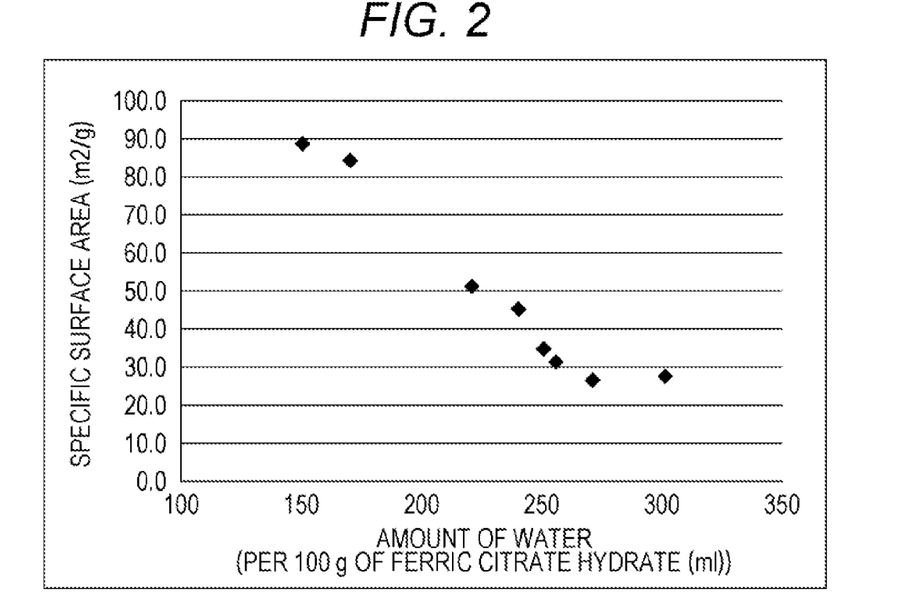
FIG. 2 is a graph showing a relation between the amount of water and the specific surface area of the obtained ferric citrate hydrate in the producing method according to non-limiting embodiments of the present invention.

Examples 11 to 17, and 32 and Comparative example 4 were performed in a manner similar to Example 1 except that the amount of water to be used was changed. The conditions and results are shown in Table 2. The part by volume (ml) of water per 100 parts by mass (g) of the ferric citrate as the material and the result of the specific surface area, which are plotted, are shown in FIG. 2.

TABLE 2

|  | Water | | Modified ferric citrate hydrate (modified material) | | | | | |
| --- | --- | --- | --- | --- | --- | --- | --- | --- |
|  | Amount used (ml) | Amount converted (ml) * | Specific surface area (m$^2$/g) | Purity (%) | Aconitic acid (%) | Itaconic acid (%) | Citraconic acid (%) | Recovery rate (%) |
| Ferric citrate as material | — | — | 30.0 | 98.06 | 0.91 | 0.12 | 0.09 | — |
| Example 1 | 68 | 170 | 84.4 | 99.95 | 0.04 | Not detected | Not detected | 90.6 |
| Example 11 | 60 | 150 | 88.8 | 99.90 | 0.08 | Not detected | Not detected | 91.0 |
| Example 12 | 88 | 220 | 51.6 | 99.96 | 0.03 | Not detected | Not detected | 87.0 |

TABLE 2-continued

| | Water | | Modified ferric citrate hydrate (modified material) | | | | | |
|---|---|---|---|---|---|---|---|---|
| | Amount used (ml) | Amount converted (ml) * | Specific surface area (m²/g) | Purity (%) | Aconitic acid (%) | Itaconic acid (%) | Citraconic acid (%) | Recovery rate (%) |
| Example 13 | 96 | 240 | 45.6 | 99.96 | 0.03 | Not detected | Not detected | 84.4 |
| Example 14 | 100 | 250 | 35.1 | 99.96 | 0.03 | Not detected | Not detected | 82.3 |
| Example 15 | 102 | 255 | 31.7 | 99.96 | 0.03 | Not detected | Not detected | 81.0 |
| Example 16 | 108 | 270 | 27.1 | 99.96 | 0.03 | Not detected | Not detected | 78.1 |
| Example 17 | 120 | 300 | 27.8 | 99.96 | 0.03 | Not detected | Not detected | 75.4 |
| Example 32 | 140 | 350 | 20.2 | 99.84 | 0.11 | 0.01 | 0.01 | 70.3 |
| Comparative example 4 | 52 | 130 | Ferric citrate was not dissolved | | | | | |

* Per 100 g of ferric citrate monohydrate converted from ferric citrate as material

Examples 18 to 21

Examples 18 to 21 were performed in a manner similar to Example 1 except that the amount of anhydrous citric acid and the amount of water to be used were changed. The conditions and results are shown in Table 3.

TABLE 3

| | Anhydrous citric acid | | Water | | Modified ferric citrate hydrate (modified material) | | | | | |
|---|---|---|---|---|---|---|---|---|---|---|
| | Amount used (g) | Amount converted (mol) *1 | Amount used (ml) | Amount converted (ml) *2 | Specific surface area (m²/g) | Purity (%) | Aconitic acid (%) | Itaconic acid (%) | Citraconic acid (%) | Recovery rate (%) |
| Ferric citrate as material | — | — | — | — | 30.0 | 98.06 | 0.91 | 0.12 | 0.09 | — |
| Example 3 | 2.92 | 0.1 | 68 | 170 | 125.2 | 99.91 | 0.08 | Not detected | Not detected | 90.3 |
| Example 18 | 2.92 | 0.1 | 60 | 150 | 135.4 | 99.87 | 0.10 | 0.01 | 0.01 | 91.1 |
| Example 19 | 2.92 | 0.1 | 88 | 250 | 54.4 | 99.95 | 0.03 | Not detected | Not detected | 81.0 |
| Example 4 | 5.84 | 0.2 | 68 | 170 | 108.9 | 99.92 | 0.06 | Not detected | Not detected | 90.5 |
| Example 20 | 5.84 | 0.2 | 60 | 150 | 122.4 | 99.89 | 0.08 | 0.01 | Not detected | 90.8 |
| Example 21 | 5.84 | 0.2 | 88 | 250 | 50.9 | 99.96 | 0.03 | Not detected | Not detected | 84.4 |

*1 Per 1 mole of ferric citrate monohydrate converted from ferric citrate as material
*2 Per 100 g of ferric citrate monohydrate converted from ferric citrate as material

Example 22

Example 22 was performed in a manner similar to Example 1 except that acetone was dripped to the solution in which the ferric citrate as the material was dissolved. As a result, the crystal adhered to the wall surface of the vessel (scaling) and about 4.5 g of ferric citrate hydrate was not isolated, and 30.3 g of the modified ferric citrate hydrate was obtained. If the molecular weight of ferric citrate monohydrate is 262.96, it is 115.2 mmol, and the yield calculated based on the mole number of the converted ferric citrate monohydrate as the material was 75.8%. The specific surface area of the ferric citrate hydrate was 72.5 m²/g. In addition, the HPLC purity of the ferric citrate hydrate was 99.87%, and the aconitic acid was 0.08%, the citraconic acid was 0.01%, the itaconic acid was not detected, and the other impurities were 0.02% at maximum.

Example 23

The wet material of the ferric citrate hydrate was obtained by a method similar to that of Example 1. To 118.3 g of the obtained wet material, 400 mL of acetone was added and the mixture was stirred for 30 minutes at 20 to 30° C. The crystal was separated by centrifugal separation and the crystal was subjected to reslurry cleaning twice with 40 mL of acetone. The wet material obtained after the cleaning had a water content of 11.6% and an acetone content of 58.4%, and the water content per 100 parts by mass of the anhydride converted from the ferric citrate hydrate was 38.7 parts by mass. The obtained low water content wet material was dried for 15 hours at 30° C. under reduced pressure, and thus 35.5 g of the modified ferric citrate hydrate was obtained. If the molecular weight of ferric citrate monohydrate is 262.96, it is 135.0 mmol, and the yield calculated based on the mole number of the converted ferric citrate monohydrate as the material was 88.7%. The BET specific surface area of the ferric citrate hydrate by a nitrogen adsorption method was 91.4 m²/g. In addition, the HPLC purity of the ferric citrate hydrate was 99.96%, and the aconitic acid was 0.02%, the citraconic acid and the itaconic acid were not detected, and the other impurities were 0.01% or less at maximum.

Examples 24 and 25

Examples 24 and 25 were performed in a manner similar to Example 23 except that the amount of acetone or the water content in acetone were changed as shown in Table 4. The results are shown in Table 4.

TABLE 4

| | Acetone | | | Ferric citrate before drying (wet material) | | | Modified ferric citrate hydrate (modified material) *3 | | | |
|---|---|---|---|---|---|---|---|---|---|---|
| Example | Amount used (mL) | Amount converted (ml) *1 | Water content (%) | Water content (%) | Acetone content (%) | Water content (part by mass) *2 | Specific surface area (m²/g) | Purity (%) | Aconitic acid (%) | Recovery rate (%) |
| Ferric citrate as material | — | — | — | — | — | — | 30.0 | 98.06 | 0.91 | — |
| Example 1 | — | — | — | 13.2 | 59.2 | 47.8 | 84.4 | 99.95 | 0.03 | 90.6 |
| Example 23 | 400 | 1000 | 0.1 | 11.6 | 58.4 | 38.7 | 91.4 | 99.96 | 0.02 | 88.7 |
| Example 24 | 72 | 180 | 0.1 | 12.2 | 58.9 | 42.2 | 89.5 | 99.96 | 0.03 | 88.4 |
| Example 25 | 400 | 1000 | 1.5 | 12.6 | 59.2 | 44.7 | 84.6 | 99.97 | 0.02 | 87.5 |

*1 Per 100 g of ferric citrate monohydrate converted from ferric citrate as material
*2 Per 100 parts by mass of pure content of ferric citrate monohydrate
*3 Neither itaconic acid nor citraconic acid were detected from the modified ferric citrate hydrate (modified material) in Examples 1 and 23 to 25

Examples 26 and 27

Examples 26 and 27 were performed in a manner similar to Example 1 except that the ferric citrate as the material was changed to 4000 g and the amount of anhydrous citric acid, water, and acetone to be used was changed to satisfy the ratio similar to that in Example 1. The conditions and the results are shown in Table 5. The average value of the results and the relative standard deviation in Examples 1, 26, and 27 are also shown.

TABLE 5

| | | Ferric citrate before drying (wet material) | | | Modified ferric citrate hydrate (modified material) *2 | | | |
|---|---|---|---|---|---|---|---|---|
| Example | Ferric citrate (crude material) (g) | Water content (%) | Acetone content (%) | Water content (part by mass) *1 | Specific surface area (m²/g) | Purity (%) | Aconitic acid (%) | Recovery rate (%) |
| Ferric citrate as material | — | — | — | — | 30.0 | 98.06 | 0.91 | — |
| Example 1 | 40 | 13.2 | 59.2 | 47.8 | 84.4 | 99.95 | 0.03 | 90.6 |
| Example 26 | 4000 | 15.1 | 63.1 | 69.3 | 65.3 | 99.89 | 0.06 | 89.4 |
| Example 27 | 4000 | 14.7 | 62.9 | 65.6 | 75.7 | 99.92 | 0.04 | 91.3 |
| Average value | — | 14.3 | 61.7 | 60.9 | 75.1 | 99.92 | 0.04 | 90.4 |
| Relative standard deviation | — | 7.0 | 3.6 | 18.8 | 12.7 | 0.03 | 35.3 | 1.06 |

*1 Per 100 parts by mass of pure content of ferric citrate monohydrate
*2 Neither itaconic acid nor citraconic acid were detected from the modified ferric citrate hydrate (modified material) in Examples 1, 26, and 27

Examples 28 and 29

Examples 28 and 29 were performed in a manner similar to Example 23 except that the ferric citrate as the material was changed to 4000 g and the amount of anhydrous citric acid, water, and acetone to be used was changed to satisfy the ratio similar to that in Example 23. The conditions and the results are shown in Table 6. The average value of the results and the relative standard deviation in Examples 23, 28, and 29 are also shown.

TABLE 6

| Example | Ferric citrate before drying (wet material) | | | | Modified ferric citrate hydrate (modified material) *2 | | | |
|---|---|---|---|---|---|---|---|---|
| | Ferric citrate (crude material) (g) | Water content (%) | Acetone content (%) | Water content (part by mass) *1 | Specific surface area ($m^2/g$) | Purity (%) | Aconitic acid (%) | Recovery rate (%) |
| Ferric citrate as material | — | — | — | — | 30.0 | 98.06 | 0.91 | — |
| Example 23 | 40 | 11.6 | 58.4 | 38.7 | 91.4 | 99.96 | 0.02 | 88.7 |
| Example 28 | 4000 | 11.7 | 59.0 | 39.9 | 91.0 | 99.97 | 0.01 | 88.4 |
| Example 29 | 4000 | 11.8 | 58.5 | 39.7 | 91.2 | 99.98 | 0.01 | 90.2 |
| Average value | — | 12.0 | 56.7 | 38.4 | 90.8 | 99.97 | 0.01 | 89.1 |
| Relative standard deviation | — | 3.8 | 2.6 | 2.2 | 0.9 | 0.01 | 43.3 | 1.08 |

*1 Per 100 parts by mass of pure content of ferric citrate monohydrate
*2 Neither itaconic acid nor citraconic acid were detected from the modified ferric citrate hydrate (modified material) in Examples 23, 28, and 29

Comparative Example 2

Comparative example 2 was performed in a manner similar to Example 1 except that acetone was replaced by ethyl acetate. As a result, the solution in which the ferric citrate as the material was dissolved was dripped into ethyl acetate, and the mixture was stirred for 1 hour at 20 to 30° C. In this case, the ferric citrate hydrate was not precipitated.

Comparative Example 3

Comparative example 3 was performed in a manner similar to Example 1 except that acetone was replaced by diethyl ether. As a result, the solution in which the ferric citrate as the material was dissolved was dripped into diethyl ether, and the mixture was stirred for 1 hour at 20 to 30° C. In this case, the ferric citrate hydrate was not precipitated.

Examples 33 and 34

Examples 33 and 34 were performed in a manner similar to Example 25 except that the ferric citrate as the material was changed to 40000 g and the amount of anhydrous citric acid, water, and acetone to be used was changed to satisfy the ratio similar to that in Example 25. The conditions and the results are shown in Table 7. The average value of the results and the relative standard deviation in Examples 25, 33, and 34 are also shown. The citraconic acid and the itaconic acid were not detected.

TABLE 7

| | Acetone | | | Ferric citrate before drying (wet material) | | | Modified ferric citrate hydrate (modified material) *3 | | | |
|---|---|---|---|---|---|---|---|---|---|---|
| | Amount used (ml) | Amount converted (ml) *1 | Water content (%) | Water content (%) | Acetone content (%) | Water content (part by mass) *2 | Specific surface area ($m^2/g$) | Purity (%) | Aconitic acid (%) | Recovery rate (%) |
| Ferric citrate as material | — | — | — | — | — | — | 30.0 | 98.06 | 0.91 | — |
| Example 1 | — | — | — | — | — | — | 84.4 | 99.95 | 0.03 | 90.6 |
| Example 25 | 400 | 1000 | 1.5 | 12.6 | 59.2 | 44.7 | 91.5 | 99.97 | 0.02 | 87.5 |
| Example 33 | 40000 | 1000 | 1.5 | 16.4 | 47.1 | 44.9 | 86.3 | 99.96 | 0.02 | 84.5 |
| Example 34 | 40000 | 1000 | 1.5 | 12.9 | 56.8 | 42.6 | 88.9 | 99.97 | 0.01 | 88.2 |
| Average value | — | — | — | 14.0 | 54.4 | 44.1 | 88.9 | 99.97 | 0.02 | 86.7 |
| Standard deviation | — | — | — | 2.11 | 6.41 | 1.29 | 2.60 | 0.01 | 0.01 | 1.97 |

*1 Per 100 g of ferric citrate monohydrate converted from ferric citrate as material
*2 Per 100 parts by mass of pure content of ferric citrate monohydrate
*3 Neither itaconic acid nor citraconic acid were detected from the ferric citrate hydrate (modified material) in Examples 1, 30, and 31

Examples 35 to 38

Examples 35 to 38 were performed in a manner similar to Example 1 except that acetone was replaced by methanol, ethanol, 2-propanol, or acetonitrile. The conditions and the results are shown in Table 8.

TABLE 8

|  |  | Modified ferric citrate hydrate (modified material) | | | | | |
| --- | --- | --- | --- | --- | --- | --- | --- |
|  | Solvent Kind | Specific surface area ($m^2/g$) | Purity (%) | Aconitic acid (%) | Itaconic acid (%) | Citraconic acid (%) | Recovery rate (%) |
| Example 1 | Acetone | 84.4 | 99.95 | 0.03 | Not detected | Not detected | 90.6 |
| Example 35 | Methanol | 72.1 | 98.72 | 0.26 | 0.05 | 0.03 | 72.3 |
| Example 36 | Ethanol | 128.9 | 99.85 | 0.06 | 0.02 | 0.01 | 80.4 |
| Example 37 | 2-propanol | 140.5 | 99.91 | 0.04 | 0.01 | 0.01 | 85.9 |
| Example 38 | Acetonitrile | 19.4 | 99.91 | 0.03 | 0.01 | 0.01 | 88.4 |

Examples 39 to 42, Comparative Example 5

Examples 39 to 42 and Comparative example 5 were performed in a manner similar to Example 1 except that acetone was replaced by a mixed solvent of acetone and a non-water-soluble organic solvent 2-butanone. The conditions and the results are shown in Table 9.

TABLE 9

|  | Acetone | | 2-butanone | | Modified ferric citrate hydrate (modified material) | | | | | |
| --- | --- | --- | --- | --- | --- | --- | --- | --- | --- | --- |
|  | Amount used (mL) *1 | Amount converted (ml) *2 | Amount used (mL) *1 | Amount converted (ml) *2 | Specific surface area ($m^2/g$) | Purity (%) | Aconitic acid (%) | Itaconic acid (%) | Citraconic acid (%) | Recovery rate (%) |
| Ferric citrate as material | — | — | — | — | 30.0 | 98.06 | 0.91 | 0.12 | 0.09 | — |
| Example 1 | 800 | 200 | 0 | 0 | 84.4 | 99.95 | 0.03 | Not detected | Not detected | 90.6 |
| Example 39 | 400 | 100 | 400 | 100 | 58.4 | 99.94 | 0.04 | Not detected | Not detected | 82.7 |
| Example 40 | 500 | 125 | 300 | 75 | 68.3 | 99.96 | 0.02 | Not detected | Not detected | 84.6 |
| Example 41 | 600 | 150 | 200 | 50 | 76.3 | 99.93 | 0.04 | Not detected | Not detected | 85.3 |
| Example 42 | 700 | 175 | 100 | 25 | 79.8 | 99.95 | 0.03 | Not detected | Not detected | 88.9 |
| Comparative example 5 | 0 | 0 | 800 | 200 | Ferric citrate hydrate was not precipitated (layer separation) | | | | | |

*1 Water-soluble organic solvent of 40/800 in the amount of use in the table was used in the cleaning of crystal
*2 Per 100 g of ferric citrate monohydrate converted from ferric citrate as material

The invention claimed is:

1. Ferric citrate hydrate having a BET specific surface area of more than 50 $m^2/g$, and 140 $m^2/g$, or less by a nitrogen adsorption method.

2. The ferric citrate hydrate according to claim 1, wherein a high-performance liquid chromatography purity of an aconitic acid is 0.01% to 0.26%.

3. The ferric citrate hydrate according to claim 1, wherein a bulk density is 1.0 $g/cm^3$.

4. A method for producing the ferric citrate hydrate according to claim 1, the method comprising a step 1 of bringing a solution containing water, citric acid, and ferric citrate as a material, and a water-soluble organic solvent into contact with each other.

5. The method for producing the ferric citrate hydrate according to claim 4, the method further comprising a step 1a of preparing the solution by dissolving the ferric citrate as the material or hydrate thereof into a citrate aqueous solution.

6. The method for producing the ferric citrate hydrate according to claim 4, wherein the water-soluble organic solvent contains at least ketone or alcohol.

7. The method for producing the ferric citrate hydrate according to claim 4, wherein an amount of the water that is used is 150 to 300 mL per 100 g of ferric citrate monohydrate converted from the ferric citrate as the material or the hydrate thereof.

8. The method for producing the ferric citrate hydrate according to claim 4, wherein an amount of the citric acid that is used is 0.05 to 1.0 moles per 1 mole of the ferric citrate monohydrate converted from the ferric citrate as the material or the hydrate thereof.

9. The method for producing the ferric citrate hydrate according to claim 4, wherein an amount of the water-soluble organic solvent that is used is 300 to 4000 mL per 100 g of the ferric citrate monohydrate converted from the ferric citrate as the material or the hydrate thereof.

10. The method for producing the ferric citrate hydrate according to claim 4, wherein the solution is dripped into the water-soluble organic solvent.

11. The method for producing the ferric citrate hydrate according to claim 4, wherein a suspension including the modified ferric citrate hydrate is obtained in the step 1, the method further comprising a step 2 of obtaining a low water content wet material of the ferric citrate hydrate containing 5 to 45 parts by mass of water per 100 parts by mass of anhydride converted from the ferric citrate hydrate from the suspension, and then drying the low water content wet material.

12. The method for producing the ferric citrate hydrate according to claim 11, wherein in the step 2, the low water content wet material is obtained in a manner that, after the wet material of the ferric citrate hydrate is obtained by separating the suspension into solid and liquid, the wet material is dispersed in the water-soluble organic solvent.

* * * * *